US010213379B2

(12) United States Patent
Miragaya et al.

(10) Patent No.: US 10,213,379 B2
(45) Date of Patent: Feb. 26, 2019

(54) FORMULATIONS FOR THE RECTAL ADMINISTRATION OF THROMBOLYTICALLY-ACTIVE AGENTS

(75) Inventors: Maria Acelia Marrero Miragaya, Ciudad de la Habana (CU); Ana Aguilera Barreto, Playa Ciudad de la Habana (CU); Lisette Gonzalez Chavez, Ciudad de la Habana (CU); Eduardo Martinez Diaz, Ciudad Habana (CU); Beatriz Torrez Cabrera, Ciudad Habana (CU); Karelia Cosme Diaz, Ciudad de la Habana (CU); Milesa Yeni Sarmiento Mayea, Ciudad Habana (CU); Luciano Francisco Hernandez Marrero, Ciudad de la Habana (CU); Beatriz Tamargo Santos, Ciudad Habana (CU)

(73) Assignee: CENTRO DE INGENIERIA GENETICA Y BIOTECHNOLOGIA, Ciudad de la Habana (CU)

( * ) Notice: Subject to any disclaimer, the term of this patent is extended or adjusted under 35 U.S.C. 154(b) by 1469 days.

(21) Appl. No.: 10/540,296

(22) PCT Filed: Dec. 22, 2003
(Under 37 CFR 1.47)

(86) PCT No.: PCT/CU03/00020
§ 371 (c)(1),
(2), (4) Date: Jan. 20, 2006

(87) PCT Pub. No.: WO2004/058219
PCT Pub. Date: Jul. 15, 2004

(65) Prior Publication Data
US 2007/0166298 A1    Jul. 19, 2007

(30) Foreign Application Priority Data
Dec. 27, 2002 (CU) .................................. 2002-0336

(51) Int. Cl.
*A61K 9/02* (2006.01)
*A61K 9/00* (2006.01)
*A61K 38/16* (2006.01)

(52) U.S. Cl.
CPC .............. *A61K 9/0031* (2013.01); *A61K 9/02* (2013.01); *A61K 38/166* (2013.01)

(58) Field of Classification Search
CPC ....... A61K 38/166; A61K 9/02; A61K 9/0031
USPC ..................................................... 424/94.64
See application file for complete search history.

(56) References Cited

U.S. PATENT DOCUMENTS

| 4,944,943 | A | * | 7/1990 | Eschenfelder et al. | ..... 424/94.64 |
| 5,098,707 | A | * | 3/1992 | Baldwin et al. | ........... 424/94.64 |
| 5,720,962 | A | * | 2/1998 | Ivy et al. | ....................... 424/401 |
| 5,837,688 | A | * | 11/1998 | Gelfand | ..................... 424/94.64 |
| 6,440,947 | B1 | | 8/2002 | Barron et al. | |

FOREIGN PATENT DOCUMENTS

| EP | 0340933 A2 | 11/1989 | |
| EP | 0672659 A1 | 9/1995 | |
| WO | WO 01/22935 A1 | * 4/2001 | ............... A61K 9/06 |

OTHER PUBLICATIONS

Miller et al., 1959, Proceedings of the Royal Society of Medicine, 52, Suppl 1, 93-95.*
Van Breda, et al., Radiology, 1987, 165, 109-111.*
"Systemic." Merriam-Webster.com. Merriam-Webster, accessed on web. Sep. 26, 2016, 8 pages.*
Kakkar, VV, et al., Treatment of Deep-Vein Thrombosis with Streptokinase, 1969, Brit. J. Surg., 56, 178-183.*
Sumi et al., "Activation of Plasma Fibrinolysis After Intrarectal Administration of High Molecular Urokinase and Its Derivative", Acta Haemat, vol. 70, 289-295 (1983).
MacKay et al., "Peptide Drug Delivery; Colonic and Rectal Absorptions", Advanced Drug Delivery Reviews, vol. 28, 253-273 (1997).
Yamamoto A. et al., "Rectal drug delivery systems Improvement of rectal peptide absorption by absorption enhancers, protease inhibitors and chemical modification," Advanced Drug Delivery Reviews, vol. 28, No. 2, Nov. 10, 1997 , pp. 275-299(25).
Nisar PJ et al., "Managing haemorrhoids." BMJ. Oct. 11, 2003;327(7419):847-51.
Bachmann F., "Development of antibodies against perorally and rectally administered streptokinase in man." J Lab Clin Med. Aug. 1968;72(2):228-38.
Wu et al., "Engineering of plasmin-resistant forms of streptokinase and their production in Bacillus subtilis: Streptokinase with longer functional half-life," Appl Environ Microbiol. Mar. 1998; 64(3): 824-829.
Castellanos-Serra et al., "Inhibition of unwanted proteolysis during sample preparation: evaluation of its efficiency in challenge experiments," Electrophoresis. Jun. 2002;23(11):1745-53.

* cited by examiner

*Primary Examiner* — Soren Howard
*Assistant Examiner* — Paul D. Pyla
(74) *Attorney, Agent, or Firm* — Hoffmann & Baron, LLP (57) ABSTRACT

Pharmaceutical formulations in suppository form, containing thrombolytic agents, which are able to penetrate rectal mucous, for the treatment of acute hemorrhoid diseases and/or diseases of thrombotic origin.

3 Claims, 7 Drawing Sheets

External thrombosed hemorrhoidal package

Response at 4th treatment day with tPA suppository.

Figure. 7

External thrombosed hemorrhoidal package

Response at 4th treatment day with SKr suppository.

FORMULATIONS FOR THE RECTAL ADMINISTRATION OF THROMBOLYTICALLY-ACTIVE AGENTS

This application is a U.S. National Phase Application of International Application No. PCT/CU2003/000020 filed on Dec. 22, 2003. The specification of International Application No. PCT/CU2003/000020 is hereby incorporated by reference.

This application asserts priority to Cuban Application No. CU 2002-0336 filed on Dec. 27, 2002. The specification of Cuban application No. CU 2002-0336 is hereby incorporated by reference.

FIELD OF THE INVENTION

The present invention is related to the field of biotechnology, medical sciences and pharmaceutical industry. It is mainly aimed at obtaining formulations for mucosal administration. These formulations contain a thrombolytic agent of peptide or proteic origin as active ingredient and pharmaceutical excipients, such as protease inhibitors, absorption enhancers, stabilizing agents, and others.

Thrombolytic agents used in this invention include streptokinase (SK), tissue plasminogen activator, without discarding the feasibility of using any other molecule with similar thrombolytic features.

BACKGROUND OF THE INVENTION

Hemorrhoids is one of the rectal pathologies with the highest worldwide incidence, having a prevalence rate of 4% in the United States and United Kingdom (Johanson J F, Sonnenberg A. The prevalence of hemorrhoids and chronic constipation, an epidemiological study. Gastroenterology 1990; 98:380). Hemorrhoids are abnormally swollen veins in the rectum and anus. Hemorrhoids are abnormally large or symptomatic conglomerates of blood vessels, supporting tissues, and overlying mucous membrane or anorectal skin venous swelling of the venous plexus of the rectal or anus mucous. It is called internal hemorrhoids when the upper plexus veins are damaged; they are located over the anal canal and are covered with mucous. The lower plexus veins are located below the region where anus and rectum converge and are covered with external skin. The drainage system of this zone lacks valves and for this reason the erect position of man rises pressure inside hemorrhoid veins, predisposing condition to hemorrhoidal disease. A complication of hemorrhoid may be produced due to its strangulation that develops a dark color as a result of underlying thrombosis.

There are many formulations in the form of suppositories or rectal ointments for local application, for the treatment of this pathology. These preparations contain anesthetics, anti-inflammatory, or anti-itching, such as ERCAL, SHERIPROCT, ULTRAPROCT, XYLOPROCT, PROCTAXID, PROCTOGLYVENOL (Rosenstein E. Pharmaceutical specialty Dictionary. Fortieth first edition 1995, 778, 1539, 1730, 1798, 1437, 1436). The main action of aforementioned formulations is a decrease in swelling and reduction of pain.

Different clinical studies have been currently carried out using vasodilators (topical nifedipine and anticoagulants such as heparin cream, which have shown some effectiveness and adverse events in the treatment of this disease (Perrofti P, Antropoli C, Molino D, De Stefano G, Antropoli M. Conservative treatment of acute thrombosed external hemorrhoids with topical nifedipine, (Dis Colon Rectum 2001 44(3):405-409)).

Besides, there are other treatments that are used in hemorrhoids (grade I and II) such as sclerosant injections, photocoagulation, hemorrhoidectomy, cryosurgery and LASER. But these treatments also have disadvantages since specialized personnel and equipment are required and attendance to medical centers is obligatory.

Sometimes complications may occur in grade III and IV hemorrhoids because of thrombosis (acute hemorrhoidal disease) and the above mentioned drugs and treatments do not cure this pathology, being necessary to remove the thrombi by means of surgery (Thrombectomy) (Bleday R, Breen E. Clinical Features of hemorrhoids. Sabiston. Textbook of surgery 16 edition, 2001: 980-986). This operation in acute phase produces a lot of discomfort and inconveniences which affect the patient's quality of life, as well as some risks of post-operation complications (Goldman: Cecil Textbook of medicine 21st Ed., Chapter 143—Diseases of the rectum and anus 570-572).

A non-surgical treatment of acute hemorrhoid disease would be very advantageous since it would avoid all the above-described inconveniences, even in those cases where hemorrhoidectomy would be needed, since this type of treatment would allow the patient to undergo surgery with a better quality of life and less complications.

Thrombolytic agents have the ability to lyse thrombi and restore venous flow in the anal canal, which would be possible using agents such as tissue-type plasminogen activator (t-PA), urokinase (u-PA) and streptokinase (SK), because of its thrombolytic and anti-inflammatory effect. Mechanism of action of each one these agents is different, in the case of t-PA, ternary complex is formed with the fibrin in the clot and plasminogen, causing the activation of plasminogen that is converted into plasmin, which is the enzyme responsible for the lysis of blood clots. (Zamarron C, Lijnen H R, Collen D. Kinetics of the activation of plasminogen by natural and recombinant tissue-type plasminogen activator, J Biol Chem, 1984; 259: 2080-2083); In the case of u-PA, it is a proteolytic enzyme that acts directly on plasminogen which is responsible for fibrin clot degradation achieving thrombolytic effect (Schneider P, Bachmann F, Sauser D. Urokinase: a short review of its properties and of its metabolism. In D'Angelo A, de. Urokinase: basic and clinical aspects. London: Academic Press, 1982; 1-15). t-PA and u-PA have been used as fibrinolitic in some diseases of thrombotic origin like pulmonary embolism, deep vein thrombosis, and others by parenteral administration. (Ouriel K, Veith F J. Acute lower limb ischemia: determinants of outcome, Surgery 1998; 124:336-342 109); (Manteiga R, Souto C, Altés A, et al. Short-.course thrombolysis the first line of therapy for cardiac valve thrombosis, J Thorac Cardiovasc Surg 1998; 115:780-784). Recombinant Streptokinase (rSK) pharmacologyc effect, the same as natural SK, is the fibrinolisys activation, where the final pass in fibrinolityc cascade is the formation of plasmin increasing fibrinogen product degradation (Chesebro J H, Knatterud G, Roberts R, et al. Thrombolysis in myocardial infarction (TIMI) Trial, Phasek. A comparison between intravenous tissue plasminogen activator and intravenous Streptokinase. Clinical Findings through hospital discharge. Circulation 1987; 76:142-154).

The anti-inflammatory effects are due to the enzymatic transformation of plasminogen into plasmin cleaving fibrinogen, fibrin or both, located in inflamed zone or in the clot favoring their drainage and diminishing the inflammation and edema (Rosenstein E. Pharmaceutics specialty Dictionary de. Fortieth first edition 1995, 778, 1539, 1730, 1798, 1437, 1436). Therefore a combination in a formulation of more than one thrombolytic agent or the combination of this agent with anti-inflammatory could be obtained a better efficacy in thrombotic disease like acute hemorrhoidal disease.

Streptokinase is high molecular weight protein which nowadays is using for the treatment of acute myocardial infarction, deep vein thrombosis, permanent vascular access thrombosis and other disease with thrombotic origin. In this way is presented in different pharmaceutics form like lyophilized for parenteral use. Also it has also been used for mucosal administration, for example, VARIDASE, for edema relieve of inflammatory process or in orally administered pills. It has also been reported rectal administration with the main objective of systemic action for the treatment of hematoma re-absorption or just for comparing its concentration in the blood after rectal and oral administration (Oliven A, Gidron E. Orally and rectally administered Streptokinase. Investigation of its absorption and activity, Pharmacology 1981; 22(2): 135-138); (de Boer A G, Moolenaar F, de Leede L G, Breimer D D. Rectal drug administration: Clinical pharmacokinetic considerations, Clin Pharmacokinet 1982; 7(4): 285-311).

The use of rectal formulation mentioned in this invention which has thrombolytic agents for the treatment of acute hemorrhoidal disease, is very convenient for treating this pathology locally, it is non invasive, not painful and without complication for the patient, due to the capacity of eliminating the thrombi and inflammation of the affected zone.

DETAILED DESCRIPTION OF THE INVENTION

The main objective of this invention is to obtain pharmaceutical formulation and its application in the form of suppository, which has thrombolytic agent as raw material, in an appropriate base for treatment of hemorrhoidal disease with thrombotic origin, having account its thrombolytic and anti-inflammatory action.

In this invention we described the obtaining of a solid pharmaceutical form, elaborated for insertion in the rectal mucosa dedicated to exercise a local action. The suppositories of the present invention are elaborated by mixing an oleaginous base, with the additives as preservatives, proteases inhibitors and the presence or absence of the absorption enhancers. Constant agitation is maintained so that the mixture cools down gradually until a temperature between 30 and 40° C. is reached, allowing the incorporation of a thrombolytic agent, dispersing it by even agitation. The resulting mixture is spilled in cold molds of suppositories where the one filled is carried out in excess. This mixture is let to cool down until solidification and the excess is eliminated before the ejection of the suppositories. The suppositories are then stored to a temperature between 2 and 8° C.

The formulations in form of suppositories described in this invention have as an advantage, just local effect as thrombolytic and anti-inflammatory, without causing none of these effects to systemic level.

Thrombolytic agents to be used are: SKr (Estrada M P, Hernandez I, et al. High level expression of streptokinase in *Escherichia coli*. Biotechnology 1992; 10:1138-1142). in a concentration between 50000 and 1500000 UI/g. T-PA is the other thrombolytic agent (Harris T J R. Second-generation plasminogen activators, Protein Engineering 1987; 1(6): 449-458), in a concentration between 500000 and 50000000 UI/g, among others.

In this invention certain additives are used, such as: proteases inhibitors and absorption enhancers (Amyn P, Sayani and Yie, Chien W. Systemic Delivery of Peptides and Proteins Across Absorptive Mucosae. Critical Reviews™ in Therapeutic Drug Carrier Systems 1996; 13(12): 85-184); (Lee W T O, Ennis R D, Longenecker J P, and bengtsson P. The bioavailability of intranasal calcitonin in healthy voluntiers with and without to permeation enhancer. Pharm. Head 1994; 11: 747); (Loughuth P, Merkic H P, Amidon O R L. Oral absorption of peptides The effect of absorption site and enzyme inhibition on the systemic availability of metkephamide. Pharm Res 1994; 11:528-535); (Nakanishi K, Masukawa T, Farmhouse M, Nadai T. Improvement of the rectal bioavailability of latamoxef sodium by adjuvants following administration of to suppository. Biol Pharm Bull 1994; 17(11): 1496-500). Specifically such promoters were used as: quelant agents (0.05%-10%), tensoactives agents (0.03%-8%), sodium salts (0.01%-10%), and the sodium diclofenac (0.1-10%), with satisfactory results.

Proteases inhibitors were also selected because of their ability to inhibit the enzymes responsible for degradation of peptides in the administration area. Some inhibitors protect specific peptides and others stabilize a wide range of them. However it is necessary to keep in mind that the inhibitor does not affect the integrity of the membrane, being this, one of the main problems to face by the use of this type of substances (Nishihata T, Howard J. Absorption-promoting adjuvants: enhancing action on rectal absorption. Advanced Drug Delivery Reviews 1997; 28: 205-228). in this invention the quelant agents were used in concentrations among 0.02%-5% with good results (Sayani T O P, Kim D D, Frenkl T L, Chun I K, Wang AND J, and Chien AND W. Transmucosal delivery of enkephalins: Comparative enhancing effects of dehydrofusidates and bile salts, Sci. Tech. Pharm. Sci. (STP Pharma) 1994; 4: 470); (Chun I K and Chien AND w. Stabilization of meghionine enkephalins in various rabbit mucosal extracts by enzyme inhibitors, Inst. J. Pharm, 1995; 121: 217); (Yamamoto A, Muranishi S. Rectal drug delivery systems. Improvement of rectal peptide absorption by absorption enhancers, protease inhibitors and chemical modification. Advanced Drug Delivery Reviews 1997; 28: 275-299).

Furthermore synthetic bases are obtained by chemical methods, such as Novata and Witepsol. These bases present low melting, that's why they are quickly melt inside the rectum releasing the active principle for posterior therapeutic effect. (Faulí I Thrashes Treated C. of Pharmacy Galénica 2000, Editorial Luzón 5, S.A of Editions Madrid; 77-103, 739-774).

In the aqueous phase of the formulation preservative agents are used, like methyl and propyl parabens (0.01-5%).

The suppositories described in this invention are capable of producing thrombolytic and anti-inflammatory actions, locally in the rectal mucosa.

EXAMPLES

Example 1. Formulation of Suppositories containing SKr and tPA as Active Principle Formulation A:

Novata or Wetepsol is melt in bano de Maria at 55° C. Methyl and propyl parabeno (0.01-0.5%) is added continuously at constant agitation until a homogenous dispersion is reached. The dispersion is cool down up to 36-40° C., afterwards t-PA (500000-50000000 UI/g) is incorporated with constant agitation. The mixture is then spilled in cold molds for suppositories of 2-3 g. Suppositories are let to solidify and the excess is removed until final ejection.

Formulation B:

It is elaborated according to procedure described in A, but EDTA (0.05-10%) is also added.

Formulation B1:

It is elaborated according to procedure described in A1, but EDTA (0.05-10%) is also added.

Formulation C:

It is elaborated according to procedure described in B but sodium diclofenac (0.1-10%) is also added.

Formulation C1:

It is elaborated according to procedure described in B1 but sodium diclofenac (0.1-10%) is also added.

Formulation D:

It is elaborated according to procedure described in B, but sodium salicylate (0.01-10%) is also added.

Formulation D1:

It is elaborated according to procedure described in B1, but sodium salicylate (0.01-10%) is also added.

Formulation E:

It is elaborated according to procedure described in B, but tween 20 (0.03%-8%) is also added.

Formulation E1:

It is elaborated according to procedure described in B1, but tween 20 (0.03%-8%) is also added.

Example 2. Assessment of the Rectal Irritability of Formulations

The procedure to determine rectal irritability is carried out according to described method (PNT/TEC/0210/rectal Irritability/G. García; 1995)

They are used in the study of healthy F1, NZ & SGB albino rabbits (female), from the same line, with average weight of 2.35 kg. The animals are randomly distributed in six groups of three. Rabbits remain in quarantine for 5 days with food and water ad libitum. In each case formulations are applied every 24 hours, for 5 days in a row.

Animals were distributed as follows:

| GROUP I | Non-treated, control group |
|---|---|
| GROUPS FROM II TO VI | Treated with formulations A, B, C, D, AND respectively as in the example 1. |

Then, histopathological, macroscopic and microscopic assessment of the rabbits rectal mucous is carried out and rectal irritability index is calculated.

During and after completing the test, no evidence of macroscopic changes was observed in the rectal mucous, nor symptoms neither signs of their presence, such as edema, erythema and secretions.

Then, the microscopic assessment of the rectal tissue reaction for each one of the formulations was carried out. Parameters, such as leucocitary infiltration, vascular congestion and edema were analyzed, calculating the rectal irritation rates.

Figure 1:
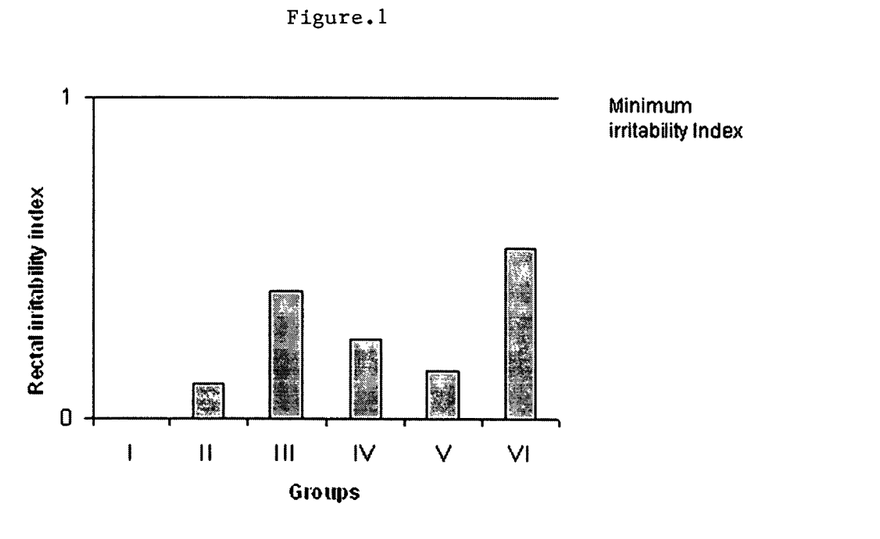
FIG. 1. Results of the rectal irritation index by groups.

The results are shown in the FIG. 1.

This study showed that prepared suppositories did not irritate the rectal mucous since, as shown in the FIG. 1, the irritability index was in the interval from 0 to 0.4 in all the cases, value that was below the index of minimum irritability.

When evaluating the formulations containing tPA as active substance, a similar result was achieved.

Example 3. Thrombosed Hemorrhoid Biomodel

The Biomodel was prepared by applying croton oil into the anus region of female rabbits F1 (N2&SGB), with average weight of 2-2.5 Kg. Cotton embedded in inducing solution (consisting of water, pyridine, diethyl ether and 6% croton oil) was introduced into the anus.

The following conditions were optimum to perform the model: An applicator embedded in 800 µL of induces solution was inserted into the anus of 12-15-weeks female rabbits for 60 seconds. The edema evolution was lineal up to 10 hours after the application, and its severity has remained almost stable during 30 hours. Macroscopic observations from 4 to 30 hours after having applied the solution shown a homogeneous and constant swelling in the region where croton oil was applied. Histological observations showed appearance of edema, infiltration of fibrin, vasodilatation, blood congestion, inflammatory cells, and necrosis in the mucosal epithelium. This model was useful for assessing the thrombolytic effect of tested products, as well as the anti-inflammatory activity of different formulations.

TABLE 1

Figure 2:
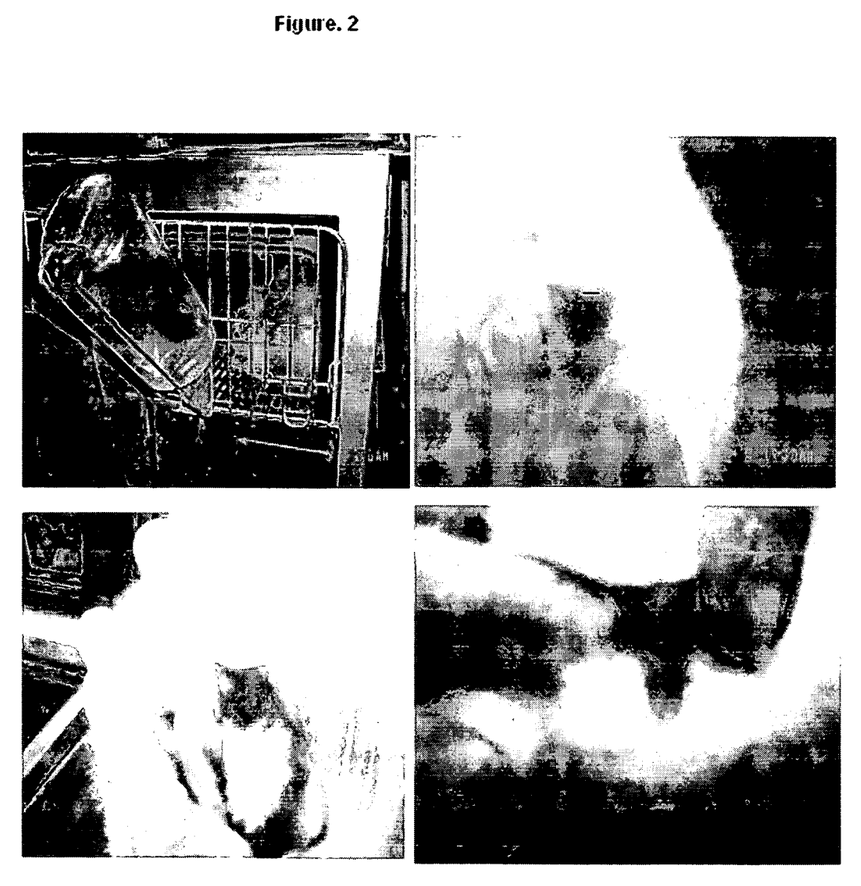
FIG. 2. Experimental generation of acute hemorrhoid disease in rabbits (0, 10 and 24 hours).
Figure 3:
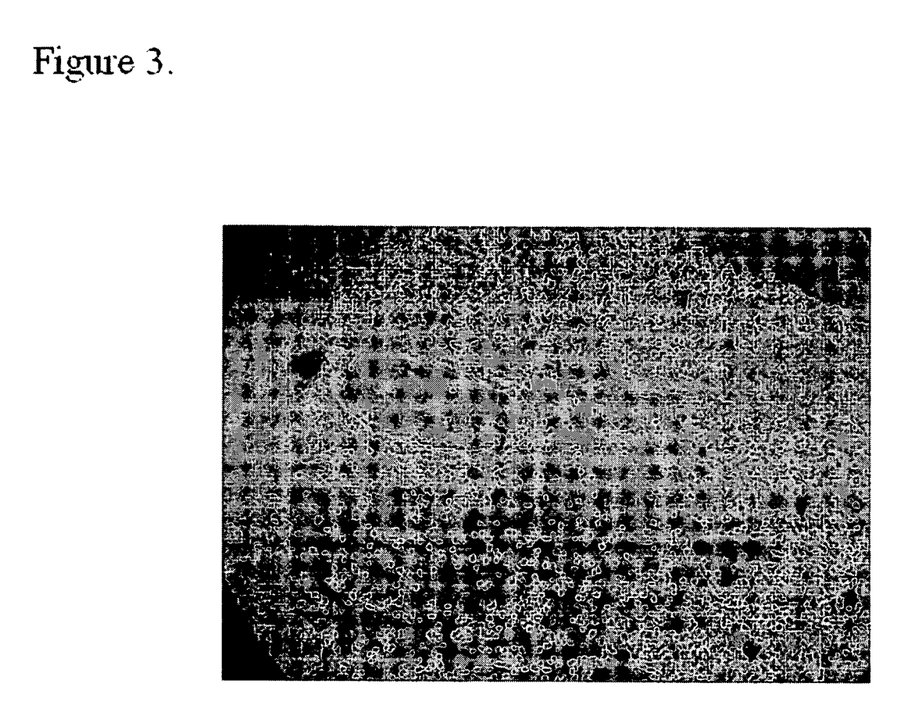
FIG. 3. Animal model for acute hemorrhoid disease using rabbits. Histology.

Clinical observations of the anus after 60-second exposure with inducing solution. See FIG. 2 and 3

| Time of observation (Hrs) | Exposure for 60 seconds |
|---|---|
| 4 | Well-defined edema, reddening |
| 10 | Congestion, edema, vesicle formation |
| 24 | Well-definition blisters, reddened erythema |
| 30 | Severe swelling, mucopurulentous secretion, blisters, presence of some ulcers |
| 48 | Moderate swelling, some blisters, and necrotic ulcers |

Example 4. Evaluation of the Thrombolytic Effect and Anti-Inflammatory Activity in Different Formulations A,A'; B,B'; C,C'; D,D'; E,E'

This assay should be followed up in details ej.3; rabbits F1 (NZxSGB), 2-3 Kg, were fastened for 12 hours before experimentation, but were allowed free access to water. In these studies, rabbits were randomly distributed in five groups of 8 animals. Before the administration of suppositories, rectal biopsies were obtained from 3 rabbit controls, in these animals, the presence of thrombus was evaluated by histological exams. Following the administration of different formulations of suppositories, blood samples were collected at baseline and 0.5, 1, 2, 4, 6, 8, 12, and 24 hours after administration. Serum was used for the quantification of C-reactive protein (CRP); citrate plasma was used for the measurement of haemostatic and coagulation parameters; prothrombin time, partial thromboplastine time, plasma concentrations of fibrinogen or fibrin degradation Products (PDF) by chromogenic substrate. Macroscopic observations and histological examinations were performed; rectal damage was scored on pathological findings according to the type and degree of mucosal damage on the rectum.

Figure 4:
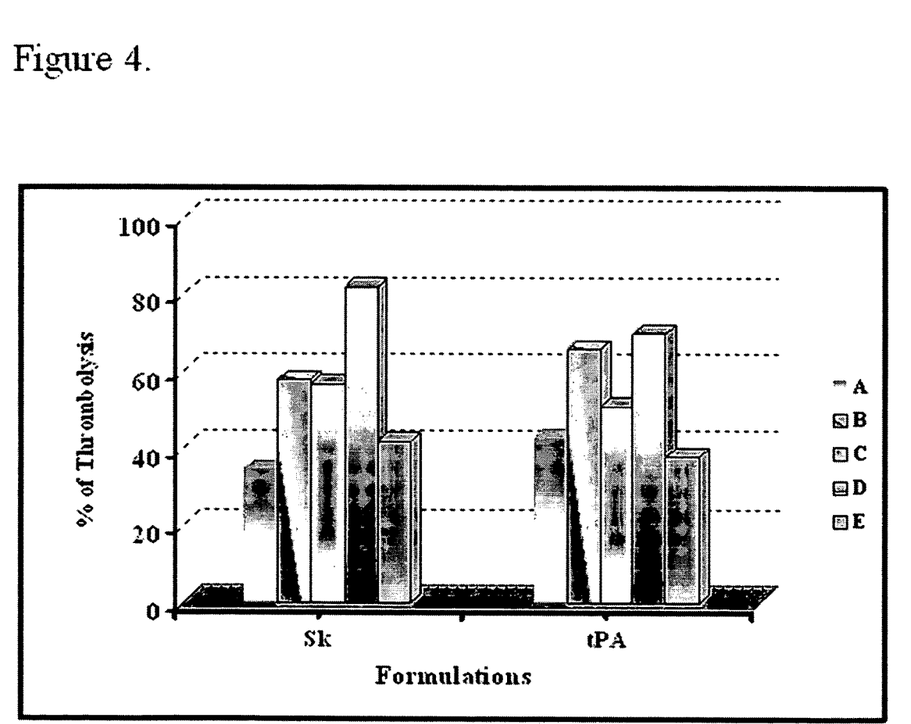
FIG. 4. Efficacy of different thrombolytic formulations in rabbits with acute hemorrhoid disease.
Figure 5:
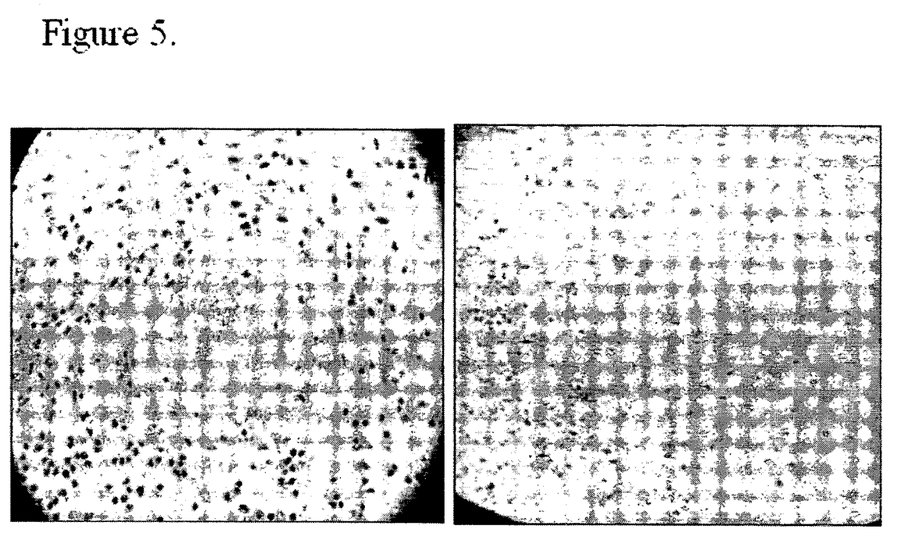
FIG. 5. Blood clot before and after the application of the formulation. Histology.

FIG. 4 shows the results to all different formulations of suppositories and pharmacological response observed to dissolve the thrombus. Generally, little of every formulation difference has been found in the effectiveness of different suppositories, but the best results were obtained with the formulations with sodium salicylate and EDTA (D,D'). The results are expressed as % of thrombolysis and both formulations were greater than 66%. All in all, our studies demonstrated that the placebo suppository does not exert lysis above blood clotting and no damage was observed in the rectal mucosa. The other control group (4) does not receive the formulations because we need to know the cross-reaction between the physiologic mechanism and the formulations to eliminate the thrombus, these data indicate that such effects are characteristic

Example 5. Clinical Study Carried Out Patients with Acute Hemorrhoids Disease The patient's symptoms carrier of thrombosed hemorrhoids is painful and uncomfortable. If it is the first episode, the medical treatment can solve the problem in a short period of time. When the episodes reappear it is necessary to do a minimal surgical treatment thrombectomy with the consequent affectation of the quality of live of the patient.

A phase II clinical trial was design with the objective of evaluating the effect of a new suppository formulation as a method for the treatment of the hemorrhoidal disease in acute phase.

In this clinical trial twenty four patient were included (Divided in three groups of eight patient each one) with diagnosis of Acute Thrombosed hemorrhoids disease. The patients were hospitalized an average of four days.

| | |
|---|---|
| Group I | Treated with SKr suppository + the usual medical treatment. |
| Group II | Treated with tPA suppository + the usual medical treatment |
| Group III | Control Group treated with the usual medical treatment that consist in: Rest in Trendelenburg position, Plenty of liquids Warm baths Use of the cushion of Kelly Pain relieve Use of oral laxatives |

The inclusion and exclusion criteria were:
Inclusion
  Age between 18 and 50 years
  Signed Informed Consent
  Pain for more than 48 hours after the appearance of the symptoms
  Hemorrhoidal package protrusion maintain for more than 48 hours
Exclusion
  Patients with contraindications for the use of thrombolitic drugs.

In the Case Report Form of each patient was included the personal information, the demographic characteristics, the disease characteristics, the evaluation of the efficacy and the adverse events of each of the treatments used in the study. The results were compared using the Chi cuadrado test and the Fisher test. Tables with the result found were created.

TABLE 2

Parameters evaluated for each one of the treatment.

| Parameters evaluated | SKr suppository (N = 8) | | tPA suppository (N = 8) | | Usual medical treatment (N = 8) | |
|---|---|---|---|---|---|---|
| | N | % | N | % | N | % |
| Clinical | | | | | | |
| Disappearance of the pain. | 7/8 | 87.5 | 6/8 | 75 | 4/8 | 50 |
| Disappearance of the (edema) | 7/8 | 87.5 | 5/8 | 62.5 | 6/8 | 75 |
| Disappearance of the itching | 7/8 | 87.5 | 7/8 | 87.5 | 5/8 | 62.5 |
| Regression of the thrombus* | 6/8 | 75 | 4/8 | 50 | 3/8 | 37.5 |
| Necessity of surgery | | | | | | |
| Trombectomy | 2 | 25 | 4 | 50 | 5 | 62.5 |
| Treatment duration (days)* | 4 | | 6 | | 10 | |
| Suspension of the treatment in study | 1 | 12.5 | 3 | 37.5 | — | — |

*$p > 0.001$

Analyzing the parameters evaluated we observe that from the clinical point of view the pain, edema and regression of the thrombus have an important value and as a matter of facts the higher percentage of healing is reached using the SKr formulation. Nevertheless, this is not statistically significant because of the scarce number of patients evaluated. In relation with the surgery treatment, minimal parameter that measure the end point of response we did observe a statistic significance (table 1). The duration of the treatment behaved in the same way, favoring the tPA and SKr formulations but for less time with the SKr formulation.

TABLE 3

Response to the treatment selected.

| Response to the treatment | SKr suppository | | tPA suppository | | usual medical treatment | |
|---|---|---|---|---|---|---|
| Total | 6 | (75%) | 4 | (50%) | 3 | (37.5%) |
| Partial | 1 | (12.5%) | 2 | (25%) | 1 | (12.5%) |
| No response | 1 | (12.5%) | 2 | (25%) | 4 | (50%) |

Figure 6:
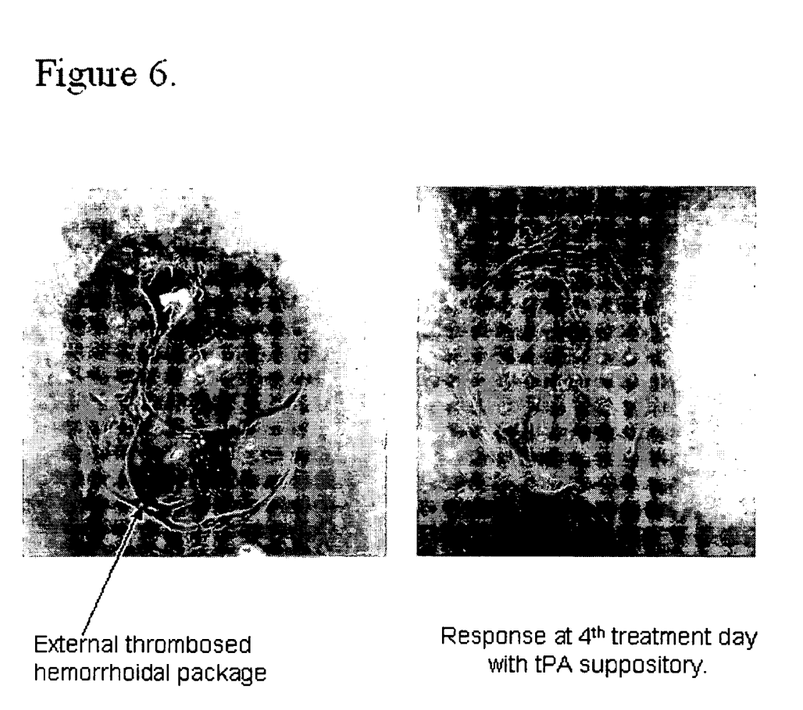
FIG. 6. Patient treated with a suppository containing tPA.
Figure 7:
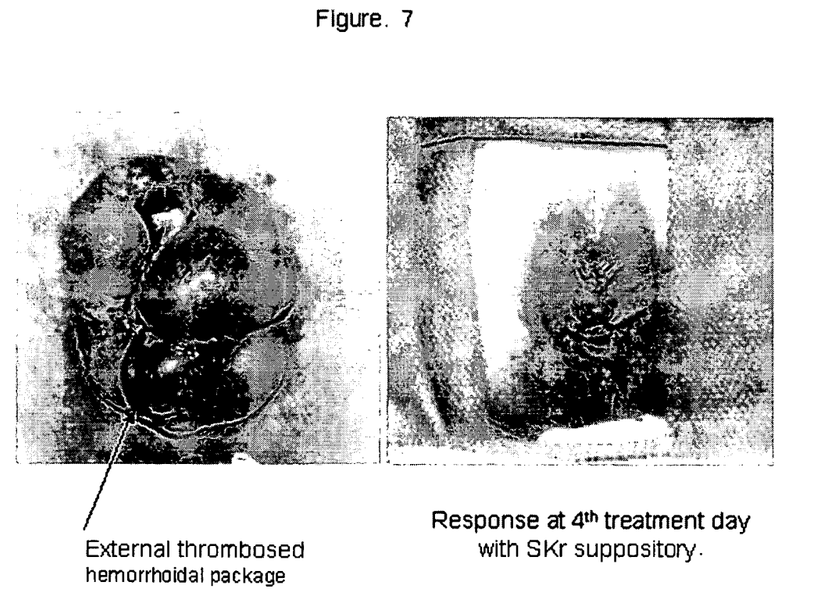
FIG. 7. Patient treated with a suppository containing SKr.

From twenty-four patients treated thirteen had total response to the treatment used (54.1%). The efficacy of the response favored significantly the SKr formulation (75%) (Table III) compare with the patients treated with tPA and the usual medical treatment. (FIGS. 6 and 7).

The results of this study showed that the use of the suppository via rectal for the acute hemorrhoidal disease improve significantly the healing and reduce the swelling.

ADVANTAGES OF THE FORMULATION OF THE INVENTION

With the formulations of the present invention it is possible to achieve the elimination of the thrombus with the consequent decrease of the inflammation and pain in the affected zone, without systemic thrombolyticeffects. Besides, this allows solving the pathology locally, in a neither painful nor invasive way. Do not require of a specialized personal or equipment for his application and it make possible the treatment of the acute hemorrhoidal disease in a non-surgical way avoiding the inconvenient inherent to this kind of treatment.

The invention claimed is:

1. A method for treating hemorrhoid disease in a human in need thereof, wherein the method consists essentially of administering to said human an effective amount of a pharmaceutical composition, said composition consisting essentially of a streptokinase (SK) and a pharmaceutically acceptable diluent, carrier or excipient, wherein the pharmaceutical composition is administered rectally as a suppository, wherein the SK is in an amount of 50,000 IU to 150,000 IU per gram of composition, wherein administration is for 4 to 6 days, wherein the treatment occurs without systemic thrombolytic effects, and wherein the pharmaceutical composition effectively treats hemorrhoid disease.

2. A method for treating hemorrhoid disease in a human in need thereof, wherein the method consists essentially of administering to said human an effective amount of a pharmaceutical composition, said composition consisting essentially of a streptokinase (SK), and ethylenediaminetetraacetic acid (EDTA) and sodium diclofenac, wherein the pharmaceutical composition is a suppository that is administered rectally, wherein the SK is in an amount of 50,000 IU to 150,000 IU per gram of composition, wherein administration is for 4 to 6 days, wherein the treatment occurs without systemic thrombolytic effects, and wherein the pharmaceutical composition effectively treats hemorrhoid disease.

3. A method for treating hemorrhoid disease in a human in need thereof, wherein the method consists essentially of administering to said human an effective amount of a pharmaceutical composition, said composition consisting essentially of a streptokinase (SK) and ethylenediaminetetraacetic acid (EDTA) and sodium salicylate, wherein the pharmaceutical composition is a suppository that is administered rectally, wherein the SK is in an amount of 50,000 IU to 150,000 IU per gram of composition, wherein administration is for 4 to 6 days, wherein the treatment occurs without systemic thrombolytic effects, and wherein the pharmaceutical composition effectively treats hemorrhoid disease.

* * * * *